(12) United States Patent
Gering et al.

(10) Patent No.: US 11,043,296 B2
(45) Date of Patent: Jun. 22, 2021

(54) SYSTEMS AND METHODS FOR SEMI-AUTOMATIC TUMOR SEGMENTATION

(71) Applicant: HealthMyne, Inc., Madison, WI (US)

(72) Inventors: David Gering, Madison, WI (US); Aaron Avery, Madison, WI (US); Jeffrey Hoffman, Madison, WI (US); Brett Young-Moxon, Madison, WI (US); Lisa Kohli, Madison, WI (US); Haley Knapp, Madison, WI (US); Roger Chylla, Madison, WI (US); Linda Peitzman, Madison, WI (US)

(73) Assignee: HealthMyne, Inc., Madison, WI (US)

(*) Notice: Subject to any disclaimer, the term of this patent is extended or adjusted under 35 U.S.C. 154(b) by 48 days.

(21) Appl. No.: 16/674,944

(22) Filed: Nov. 5, 2019

(65) Prior Publication Data
US 2020/0143934 A1 May 7, 2020

Related U.S. Application Data

(60) Provisional application No. 62/755,873, filed on Nov. 5, 2018.

(51) Int. Cl.
*G06K 9/00* (2006.01)
*G16H 30/40* (2018.01)
(Continued)

(52) U.S. Cl.
CPC .......... *G16H 30/40* (2018.01); *G06T 7/0014* (2013.01); *G06T 7/12* (2017.01); *G06T 7/174* (2017.01);
(Continued)

(58) Field of Classification Search
None
See application file for complete search history.

(56) References Cited

U.S. PATENT DOCUMENTS

2005/0027188 A1* 2/2005 Metaxas ................ A61B 5/055
600/410
2005/0111710 A1 5/2005 Gritzky et al.
(Continued)

FOREIGN PATENT DOCUMENTS

WO 2010115885 A1 10/2010
WO WO2017037832 A1 3/2017

OTHER PUBLICATIONS

International Search Report with Written Opinion for Application No. PCT/US2018/40473 dated Sep. 17, 2018, 15 pages.
(Continued)

*Primary Examiner* — Atiba O Fitzpatrick
(74) *Attorney, Agent, or Firm* — Michael Best & Friedrich LLP

(57) ABSTRACT

A method for volumetric segmentation in a plurality of planar medical images includes, receiving, at an electronic processor, the plurality of planar medical images. A boundary of a candidate structure in the plurality of medical images is generated using a segmentation model. A first planar medical image from the plurality of planar medical images is displayed on a display. A user input is received using a user interface indicating a region in the first planar medical image. A first planar contour of the candidate structure is generated. The region is compared to the boundary. Responsive to the region being at least partially within the boundary, the first planar medical image is re-displayed on the display showing the first planar contour of the structure, and a finding record for the candidate structure including the boundary is generated.

20 Claims, 5 Drawing Sheets

(51) Int. Cl.
  G06T 7/00   (2017.01)
  G06T 7/12   (2017.01)
  G06T 7/174  (2017.01)
  G06T 11/60  (2006.01)
  G06T 11/00  (2006.01)
(52) U.S. Cl.
  CPC .......... *G06T 11/008* (2013.01); *G06T 11/60* (2013.01); *G06T 2207/10088* (2013.01); *G06T 2207/20081* (2013.01); *G06T 2207/30016* (2013.01); *G06T 2207/30096* (2013.01)

(56) References Cited

U.S. PATENT DOCUMENTS

| | | | |
|---|---|---|---|
| 2006/0013482 | A1* | 1/2006 | Dawant .............. G06T 7/12 382/173 |
| 2007/0133848 | A1* | 6/2007 | McNutt ............... G06T 7/149 382/128 |
| 2008/0021502 | A1 | 1/2008 | Imielinska et al. |
| 2008/0260221 | A1 | 10/2008 | Unal et al. |
| 2008/0281182 | A1* | 11/2008 | Rabben .............. G03B 42/06 600/407 |
| 2009/0097728 | A1 | 4/2009 | Lee et al. |
| 2009/0180677 | A1 | 7/2009 | Li et al. |
| 2012/0134552 | A1* | 5/2012 | Boettger ............. G06T 7/12 382/128 |
| 2015/0078640 | A1 | 3/2015 | Guo et al. |
| 2015/0089365 | A1 | 3/2015 | Zhao et al. |
| 2016/0300351 | A1 | 10/2016 | Gazit |
| 2017/0039725 | A1 | 2/2017 | Dror et al. |
| 2017/0249744 | A1 | 8/2017 | Wang et al. |
| 2018/0146953 | A1* | 5/2018 | Jaremko ............. A61B 8/483 |
| 2020/0268251 | A1* | 8/2020 | Hao .................. A61B 5/1128 |
| 2020/0268339 | A1* | 8/2020 | Hao .................. G06T 7/73 |
| 2021/0035296 | A1* | 2/2021 | Mahrooghy .......... A61B 8/469 |

OTHER PUBLICATIONS

3D Slicer, Available at: http://www.slicer.org., website available as early as Oct. 18, 2000, 1 page.

Aerts et al., "Decoding tumour phenotype by noninvasive imaging using a quantitative radiomics approach," Nat Commun., 2014; 5(4006): 1-8.

Agam et al., "Vessel tree reconstruction in thoracic CT scans with application to nodule detection," IEEE Transactions on Medical Imaging, 2005; 24(4): 486-499.

Armato et al., "Automated lung segmentation for thoracic CT: Impact on computer-aided diagnosis," Academic Radiology, 2004; 11(9): 1011-1021.

Armato et al., "The lung image database consortium (LIDC) and image database resource initiative (IDRI): a completed reference database of lung nodules on CT scans," Medical physics, 2011; 38(2): 915-931.

Armato III, et al., "Data From LIDC-IDRI," The Cancer Imaging Archive, Available at: http://doi.org/10.7937/K9/TCIA.2015.LO9QL9SX, 2015; 3 pages.

Ben-Cohen et al., "Automated method for detection and segmentation of liver metastatic lesions in follow-up CT examinations," Journal of Medical Imaging, 2015; 2(3): 034502-034502.

Catmull, "A class of local interpolating splines," Computer Aided Geometric Design, 174; 317-326.

Clark et al., "The Cancer Imaging Archive (TCIA): maintaining and operating a public information repository," Journal of digital imaging, 2013; 26(6): 1045-1057.

Cline et al., "3D reconstruction of the brain from magnetic resonance images using a connectivity algorithm," Magnetic Resonance Imaging, 1987; 5(5): 345-352.

Dehmeshki et al., "Segmentation of pulmonary nodules in thoracic CT scans: a region growing approach," IEEE transactions on medical imaging, 2008; 27(4): 467-480.

Diciotti et al., "3-D segmentation algorithm of small lung nodules in spiral CT images," IEEE transactions on Information Technology in Biomedicine, 2008; 12(1): 7-19.

Duda et al., "Pattern classification," John Wiley & Sons, 2001.

Erickson et al., "Radiology Data from the Cancer Genome Atlas Liver Hepatocellular Carcinoma," TCGA-LIHC collection, The Cancer Imaging Archive, Available at: http://doi.org/10.7937/K9/TCIA.2016.IMMQW8UQ, 2016; 3 pages.

Frangi et al., "Multiscale vessel enhancement filtering," Int Conf Med Image Comput Comput Assist Interv., Springer Berlin Heidelberg, 1998; 130-137.

Freedman, "A reality check for IBM's AI ambitions," MIT Technology Review, Available at: https://www.technologyreview.com/s/607965/a-reality-check-for-ibms-ai-ambitions/, 2017; 19 pages.

Gering, "Recognizing Deviations from Normalcy for Brain Tumor Segmentation," MIT Ph.D. Thesis, Available at: http://people.csail.mit.edu/gering/, 2003; 189 pages.

Grady, "Random walks for image segmentation," IEEE transactions on pattern analysis and machine intelligence, 2006; 28(11): 1768-1783.

GrowCut plug-in. Available at: http://www.growcut.com, website available as early as 2008, 2 pages.

Gurcun et al., "Lung nodule detection on thoracic computed tomography images: Preliminary evaluation of a computer-aided diagnosis system," Medical Physics, 2002; 29(11): 2552-2558.

Harris, "Signify Research Market Analysis," http://signifyresearch.net/analyst-insights/quantitative-imaging-software-market-exceed-500m-2021/, 2017, 4 pages.

Holger et al., 2015. A new 2.5 D representation for lymph node detection in CT. The Cancer Imaging Archive. http://doi.org/10.7937/K9/TCIA.2015.AQIIDCNM.

Hu et al., 2001. Automatic lung segmentation for accurate quantitation of volumetric X-ray CT images. IEEE transactions on medical imaging, 20(6), pp. 490-498.

Huttenlocher et al., 1993. Comparing images using the Hausdorff distance. IEEE Transactions on pattern analysis and machine intelligence, 15(9), pp. 850-863.

Invivo DynaCAD, Available at: http://www.invivocorp.com/solutions/lung-cancer-screening/.

Jolly et al., "3D general lesion segmentation in CT," 2008 5th IEEE International Symposium on Biomedical Imaging: From Nano to Macro, Paris, 2008; 796-799.

Kapur, 1999. Model based three dimensional medical image segmentation (Doctoral dissertation, Massachusetts Institute of Technology) 123 pages.

Kotis et al., 2003. Three-dimensional segmentation and growth-rate estimation of small pulmonary nodules in helical CT images. IEEE transactions on medical imaging, 22(10), pp. 1259-1274.

Li, "Markov random field modeling in image analysis," Springer Science & Business Media 2009, 8 pages.

Lung Cancer, Available at: https://www.thoracic.org/patients/patient-resources/breathing-in-america/resources/chapter-11-lung-cancer.pdf, 2010, 12 pages.

Lung-RADS, Available at: https://www.acr.org/Quality-Safety/Resources/LungRADS, website available as early as 2014, 4 pages.

Mirada XD3, Available at: http://www.mirada-medical.com/_public/documents/1425036206_mm3540-1-usaxd3forrecisthr.pdf, 2015; 2 pages.

Nordstrom, "The Quantitative Imaging Network in Precision Medicine," In Tomography, 2016; 2(4): 239-241.

Politi et al., "Lung Cancer in the Era of Precision Medicine," In Clin Cancer Res., 2016; 21(10): 2213-2220.

Press et al. "Numerical recipes 3rd edition: The art of scientific computing," Cambridge university press, 2007; 12 pages.

Qiba CT Volumetry Technical Committee. CT Tumor Volume Change Profile—2016, Consensus Profile. Quantitative Imaging Biomarkers Alliance, Available at: http://qibawiki.rsna.org/index.php/Profiles, See especially "Checklist—CT Tumor Volumetry for Advanced Disease," Nov. 21, 2016; 2 pages.

Ross et al., "Lung extraction, lobe segmentation and hierarchical region assessment for quantitative analysis on high resolution computed tomography images," Med Image Comput Comput Assist Interv., 2009; 12(Pt 2): 690-698.

(56) References Cited

OTHER PUBLICATIONS

Roth et al., "A new 2.5 D representation for lymph node detection using random sets of deep convolutional neural network observations," Int Conf Med Image Comput Comput Assist Interv,Springer, Cham., 2014; 520-527.
Saito et al., "New algorithms for euclidean distance transformation of an n-dimensional digitized picture with applications," Pattern recognition, 2014; 27(11): 1551-1565.
Sato et al., "Three-dimensional multi-scale line filter for segmentation and visualization of curvilinear structures in medical images," Medical image analysis, 1998; 2(2): 143-168.
Seff et al., "Leveraging mid-level semantic boundary cues for automated lymph node detection," Int Conf Med Image Comput Comput Assist Interv,Springer, Cham., 2015; 53-61.
Therasse et al., "New guidelines to evaluate the response to treatment in solid tumors," Journal of the National Cancer Institute, 2000; 92(3): 205-216.
Tunali et al., "P1. 01-041 Quantitative Imaging Features Predict Response of Immunotherapy in Non-Small Cell Lung Cancer Patients," Journal of Thoracic Oncology,2017; 12(1): S474-S475.
Velazquez et al., "Volumetric CT-based segmentation of NSCLC using 3D-Slicer," Scientific reports, 2013; 3(3529): 1-7.
Vezhnevets et al., "GrowCut: Interactive multi-label ND image segmentation by cellular automata," In proc. of Graphicon, 2005; 1(4): 150-156.
Xu et al., "Automated lung nodule segmentation using dynamic programming and EM based classification," In Proc. SPIE, 2002; 4684: 666-676.
Yabroff et al., Economic Burden of Cancer in the US: Estimates, Projections and Future Research, Cancer Epidemiol Biomarkers Prev., 2014; 20(10): 2006-14.
Yan et al., "Semiautomatic segmentation of liver metastases on volumetric CT images,"Med Phys. 2015; 42(11): 6283-6293.
Yankeelov et al., "Quantitative Imaging in Cancer Clinical Trials," Clin Cancer Res. 2016; 22(2): 284-290.
Ye et al., "Shape-based computer-aided detection of lung nodules in thoracic CT images," IEEE Transactions on Biomedical Engineering, 2009; 56(7): 1810-1820.
Zhao et al., "Data From Rider_Lung CT," The Cancer Imaging Archive, Available at: http://doi.org/10.7937/K9/TCIA.2015.U1X8A5NR, 2015; 4 pages.
Zhao et al., "Evaluating variability in tumor measurements from same-day repeat CT scans of patients with non-small cell lung cancer," Radiology. 2009; 252(1): 263-72.
Zhou et al., "Automatic multiscale enhancement and segmentation of pulmonary vessels in CT pulmonary angiography images for CAD applications," Med Phys., 2007; 34(12): 4567-77.
Zhou et al., "Automatic segmentation and recognition of anatomical lung structures from high-resolution chest CT images," Comput Med Imaging Graph., Jul. 2006; 30(5): 299-313.
Zhu et al., "An effective interactive medical image segmentation method using fast growcut. In MICCAI workshop on interactive medical image computing," Int Conf Med Image Comput Comput Assist Interv., 2014; 1-9.
Zou et al., "Statistical validation of image segmentation quality based on a spatial overlap index," Academic radiology, 2004; 11(2): 178-189.
U.S. Non-Final Office Action for related U.S. Appl. No. 15/990,131 dated Jul. 11, 2019 (26 Pages).
U.S. Final Office Action for related U.S. Appl. No. 15/990,131 dated Nov. 21, 2019 (30 Pages).
Gering, "Semi-automatic Brain Tumor Segmentation by Drawing Long Axes on Multi-plane Reformat" Pre-Conference Proceedings of the 7th MICCAI BraTS Challenge, pp. 153-160, Sep. 2018.
International Search Report and Written Opinion for Application No. PCT/US2019/059897 dated Jan. 22, 2020 (14 pages).
Hamamci et al., "Tumor-Cut: Segmentation of Brain Tumors on Contrast Enhanced MR Images for Radiosurgery Applications," IEEE Transactions on Medical Imaging, 2012, 31(3):790-804.
European Patent Office Extended Search Report for Application No. 18824764.7 dated Jan. 25, 2021 (9 pages).

* cited by examiner

SYSTEMS AND METHODS FOR SEMI-AUTOMATIC TUMOR SEGMENTATION

RELATED APPLICATIONS

This application claims priority to U.S. Provisional Application No. 62/755,873, entitled "SYSTEMS AND METHODS FOR SEMI-AUTOMATIC BRAIN TUMOR SEGMENTATION," filed Nov. 5, 2018, the entire contents of which is incorporated herein by reference.

FIELD

Embodiments of the invention relate to analyzing medical images and, more particularly, to integrating offline analysis with user interaction to segment brain and other types of tumors.

BACKGROUND

Extracting quantitative variables from medical images contributes more information for decision support in management of cancer patients, helping to improve patient outcomes. Currently, radiological studies are generally limited to detection and staging along with qualitative descriptions. Quantitative descriptors are not yet in the standard of care primarily due to a lack of infrastructure and tools to derive, test, and deploy these quantitative metrics at the point-of-care for all patients.

SUMMARY

Currently available tools for quantitative analysis lack the speed, precision, and consistency required for wider clinical use. Delineating lesion boundaries correctly is time consuming and inefficient for radiologists. This can be performed by manually drawing the tumor boundary on each image slice, by semi-automatically guiding an algorithm, or by using fully automated methods. Although manual delineation offers complete control to the user, the process is time consuming and may produce variable results due to variable performance among those performing the process. In either the semi-automated or fully automated methods, manual editing is necessary to produce useable results.

In particular, embodiments described herein provide systems and methods for volumetric segmentation in a plurality of planar medical images.

In one embodiment, a system for volumetric segmentation in a plurality of planar medical images includes a display, a user interface, an electronic processor coupled to the display and the user interface, and a memory coupled to the electronic processor and storing instructions that, when executed by the electronic processor, cause the system to receive the plurality of planar medical images. A boundary of a candidate structure in the plurality of medical images is generated using a segmentation model. A first planar medical image from the plurality of planar medical images is displayed on a display. A user input is received using a user interface indicating a region in the first planar medical image. A first planar contour of the candidate structure is generated. The region is compared to the boundary. Responsive to the region being at least partially within the boundary, the first planar medical image is re-displayed on the display showing the first planar contour of the structure, and a finding record for the candidate structure including the boundary is generated.

In another embodiment, a method for volumetric segmentation in a plurality of planar medical images includes, receiving, at an electronic processor, the plurality of planar medical images. A boundary of a candidate structure in the plurality of medical images is generated using a segmentation model. A first planar medical image from the plurality of planar medical images is displayed on a display. A user input is received using a user interface indicating a region in the first planar medical image. A first planar contour of the candidate structure is generated. The region is compared to the boundary. Responsive to the region being at least partially within the boundary, the first planar medical image is re-displayed on the display showing the first planar contour of the structure, and a finding record for the candidate structure including the boundary is generated.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
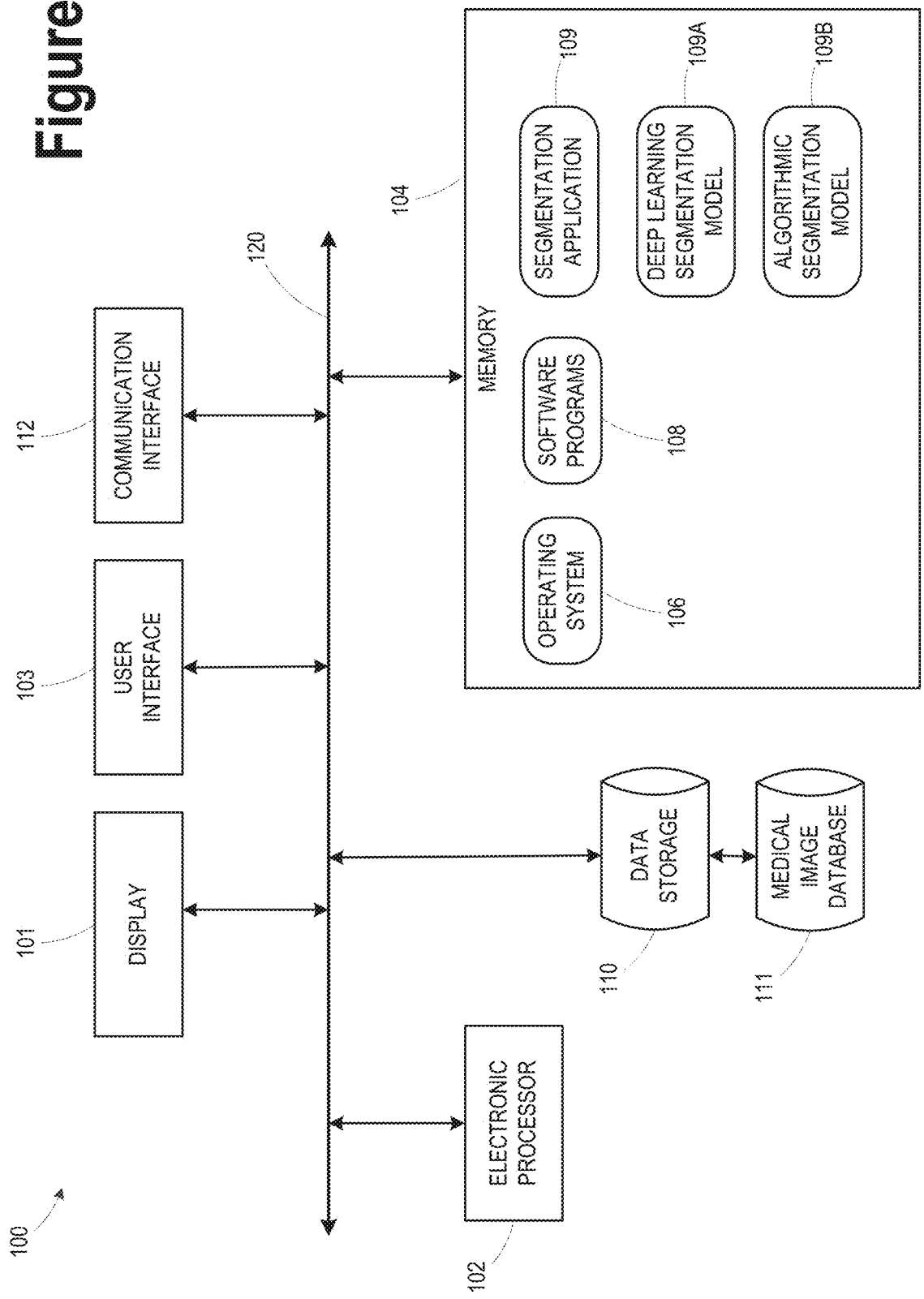
FIG. 1 is a block diagram of one embodiment of a system for performing structure segmentation in medical images, according to some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways.

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used herein, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

Also, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

Example systems and methods disclosed and contemplated herein relate to segmentation of structures in medical images. Although the following description focuses on image segmentation in a medical context, it will be appreciated that various systems, methods, and techniques disclosed herein are applicable to other domains, such as autonomous vehicles. For example, with the autonomous vehicle space, images may be segmented to identify a road centerline, a stop sign, or other findings of interested similar to findings of interest in medical images.

Fully automated segmentation, especially based on deep neural networks, has shown promising results when used to analyze magnetic resonance scans of brain tumors. However, such Computer Aided Detection (CAD) systems may produce false positive indications. Accordingly, embodiments described herein combine automated segmentation with a real-time user interface that allow a radiologist to make an initial indication regarding a finding that allows a previously identified structure generated by the CAD system to be matched to the radiologist's finding. Such embodiments provide clinical radiologists with control over the segmentation, real-time feedback, and an algorithm that is ready to run without the need to first be trained on a large database from their site. Such embodiments improve efficiency and accuracy over existing methods, including editing of a fully automated segmentation method.

Evidence from cancer researchers suggests that extraction of quantitative variables from medical images can contribute more information for decision support in management of cancer patients. Specifically, quantitative metrics can improve both diagnostic and prognostic accuracy as well as longitudinal monitoring of patient response. Criteria for monitoring radiographic brain tumor progression include the Macdonald criteria, Response Evaluation Criteria in Solid Tumors (RECIST), WHO criteria, and RANO criteria.

Volumetric contouring of a structure included in medical images provides advantages, such as inter-observer consistency, while also catering to individual preferences for accuracy and style. Consistency results from initialization strategies that are reproducible. For example, using a user may identify a structure using a straight stroke approach rather than free-form drawing, and the contouring of the structure may be performed automatically. Tailoring to individual preferences is accomplished by editing tools that may be used by a user if the initial contours are unsatisfactory. In some embodiments, there is exactly one tool in a reading room, generally applicable to all organs, yet simultaneously specialized with organ-specific features. The organ is automatically identified upon tool initialization.

FIG. 1 schematically illustrates one embodiment of a system 100 for performing segmentation of features on medical images, according to some embodiments. The system 100 may combine one or more of hardware, software, and firmware, to implement a method provided herein. In the example illustrated, the system 100 includes a display 101, an electronic processor 102, a user interface 103, a memory 104, data storage device 110, a communication interface 112 and a bus 120. As illustrated, the memory 104 may store an operating system 106 and software programs 108. The electronic processor 102 includes at least one processor or microprocessor that interprets and executes a set of instructions stored in the memory 104. In some embodiments, the software programs 108 include a segmentation application 109. In some embodiments, the electronic processor 102 includes multiple computing devices that may be distributed across multiple entities. In some embodiments, the electronic processor 102 is implemented by a virtual processor executing on a cloud-based processing service.

The user interface 103 may include one or more input devices, one or more output devices, or a combination thereof. Accordingly, in some embodiments, the user interface 103 allows a user to interact with (for example, provide input to and receive output from) the system 100. For example, the user interface 103 may include a keyboard, a cursor-control device (for example, a mouse), a touch screen, a scroll ball, a mechanical button, a display device (for example, a liquid crystal display (LCD)), a printer, a speaker, a microphone, or a combination thereof.

The memory 104 stores data used during the execution of instructions by the processor 102. The memory 104 may include volatile memory elements (for example, random access memory (RAM)), nonvolatile memory elements (for example, ROM), and combinations thereof. The memory 104 may have a distributed architecture, where various components are situated remotely from one another, but may be accessed by the electronic processor 102. The one or more programs 108 may be configured to implement the methods described herein.

The data storage device 110 may include a non-transitory, tangible, machine-readable storage medium that stores machine-readable code or instructions. In one example, the data storage device 110 stores a set of instructions detailing a method provide herein that when executed by one or more processors cause the one or more processors to perform the method. The data storage device 110 may also be a database or a database interface for storing an application module. In one example, the data storage device 110 is located external to the system 100. In some embodiments, the data storage 110 includes a medical image database 111.

The bus 120, or other component interconnection, may permit communication among the components of the system 100. The bus 120 may be, for example, one or more buses or other wired or wireless connections, as is known in the art. The bus 120 may have additional elements, which are omitted for simplicity, such as controllers, buffers (for example, caches), drivers, repeaters and receivers, or other similar components, to enable communications. The bus 120 may also include address, control, data connections, or a combination of the foregoing to enable appropriate communications among the aforementioned components.

The communication interface 112 provides the system 100 a communication gateway with one or more external networks (for example, a wireless network, the Internet, etc.). The communication interface 112 may include, for example, an Ethernet card or adapter or a wireless local area network (WLAN) card or adapter (for example, operating according to the IEEE standard 802.11a/b/g/n). The communication interface 112 may include address, control, and/or data connections to enable appropriate communications on the external network(s).

In some embodiments, the methods provided herein are performed by a software application executed by a server, and a user may access and interact with the software application using a computing device. Also, in some embodiments, functionality provided by the software application may be distributed between a software application executed by a local device and a software application executed by another electronic process or device (for example, a server) external to the local device.

Figure 2:
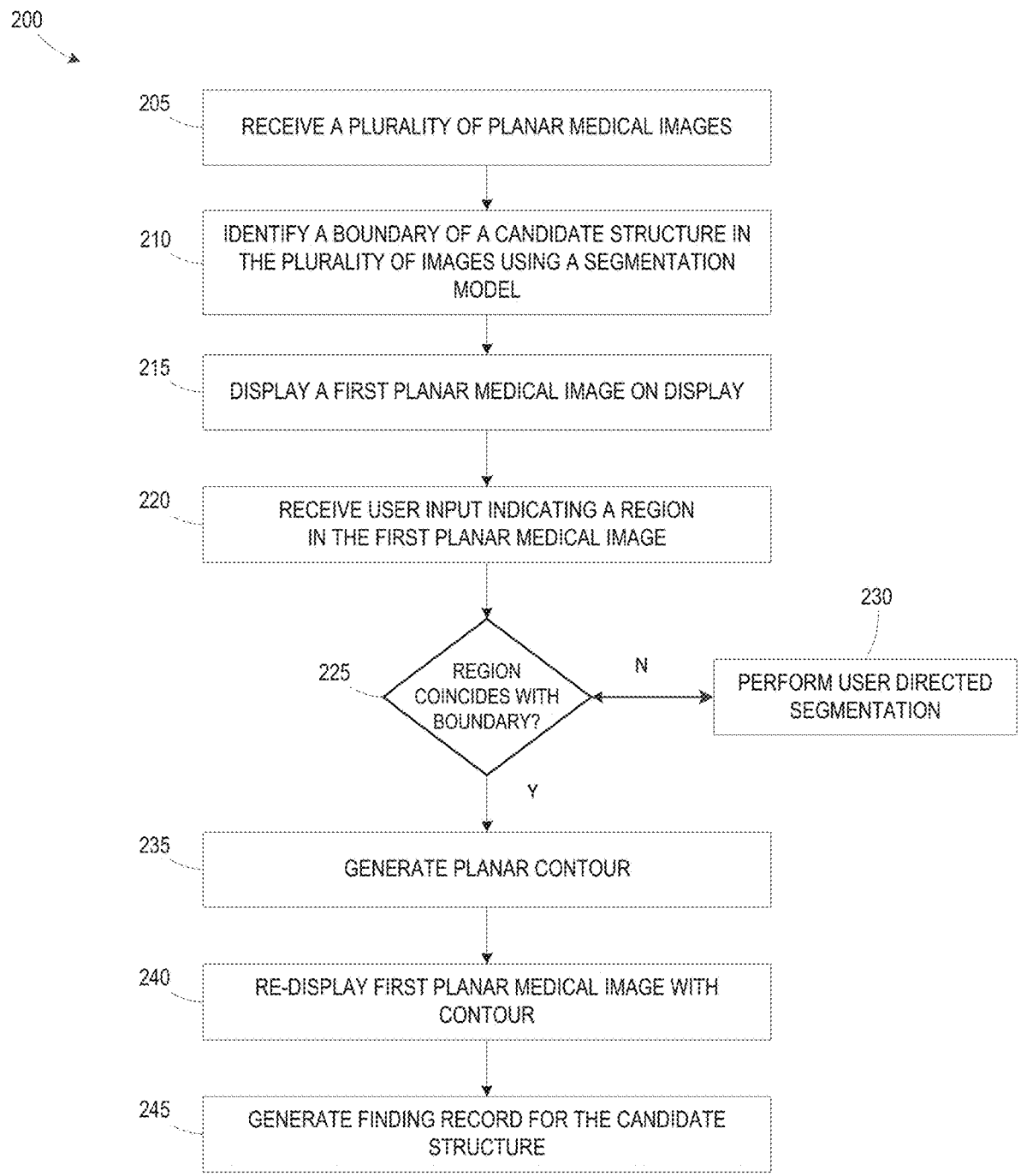
FIG. 2 illustrates a flowchart for a method of structure segmentation, according to some embodiments.

FIG. 2 illustrates a flowchart for a method 200 of structure segmentation, according to some embodiments. In block 205, a plurality of medical images is received. For example, the medical images may be generated by a scanning tool, such as a computed tomography (CT) tool, a positron emission tomography (PET) tool, a magnetic resonance imaging (MRI) tool, etc., and stored in the medical image database 111. The segmentation application 109 executed by the electronic processor 102 receives the plurality of medical images.

Figure 3:
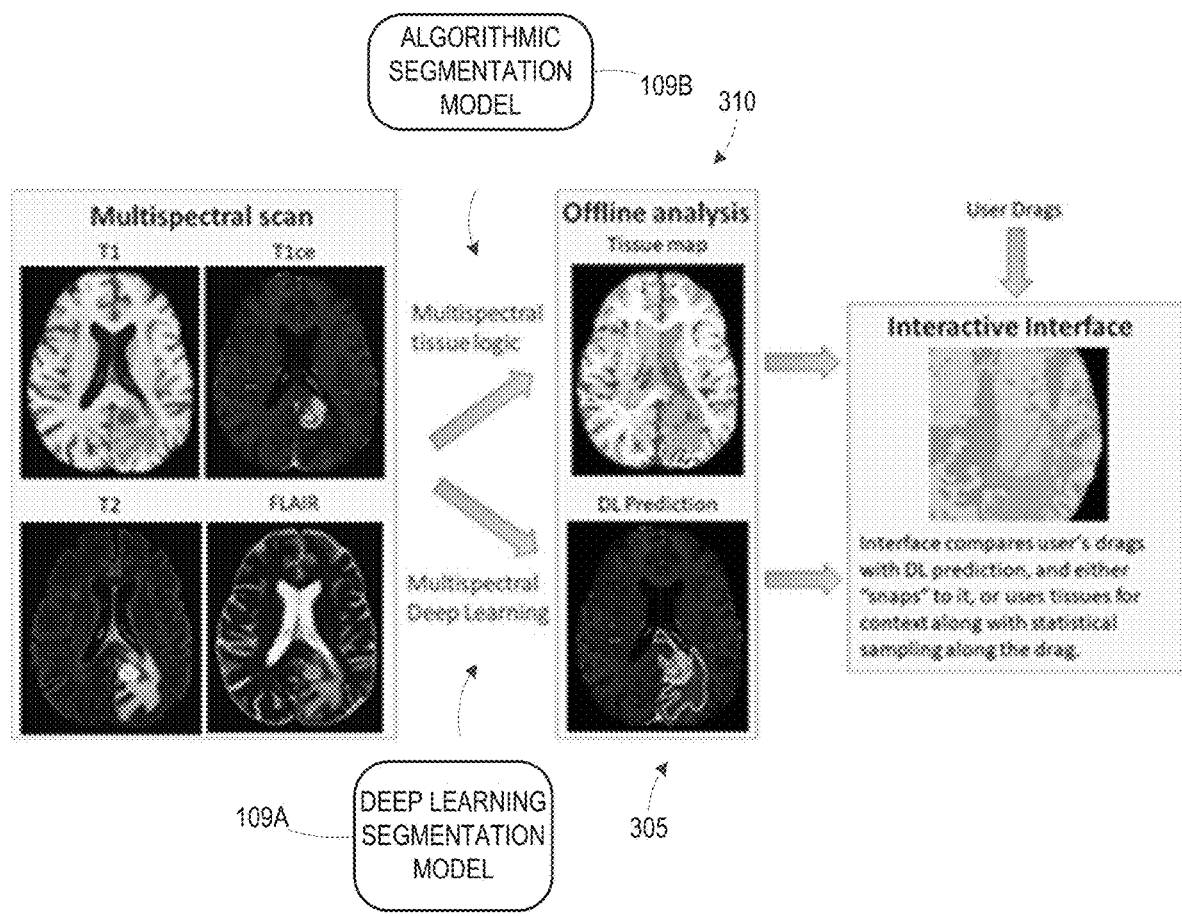
FIG. 3 illustrates a process flow for performing automatic segmentation, according to some embodiments.

In block 210, the segmentation application 109 employs one or more segmentation models to identify one or more candidate structures depicted in the plurality of medical images and generates a boundary of each candidate structure. Since segmentation models 109A, 109B are known to generate false positives, the boundaries identified by the off-line analysis using the segmentation models 109A, 109B may be referred to as boundaries for candidate structures. FIG. 3 illustrates a process flow for performing automatic segmentation by the segmentation application 109, according to some embodiments. In some embodiments, the segmentation application 109 employs a deep learning segmentation model 109A or an algorithmic segmentation model 109B, or both (see FIG. 1). In some embodiments, the segmentation models 109A, 109B are relatively computationally intensive (e.g., requiring about one minute of computing time each on a typical minicomputer). The segmentation application 109 performs the segmentation analysis off-line using the segmentation models 109A, 109B. For example, the segmentation application 109 may perform the segmentation analysis relatively soon after the medical images are generated, and prior to them being reviewed by a radiologist of other user. In this manner, the segmentation need not be performed in real time coincident with review by the radiologist. In general, the deep learning segmentation model 190A generates boundaries 305 of one or more candidate structures identified in the plurality of medical images. In some embodiments, the boundaries are three-dimensional boundaries.

In some embodiments, the plurality of images include multispectral images of the same scan region. For example, Mill data may include T1 weighted images, T2 weighted images, T1 contrast enhanced (CE) images, or fluid-attenuated inversion recovery (FLAIR) images. In some embodiments, the segmentation models 109A, 109B receive the multispectral images as inputs allowing data from the different spectrums to be factored into the segmentation. In some embodiments, the segmentation models 109A, 109B perform whole organ segmentation (e.g., whole brain segmentation) and partitioning of the tissue into its constituent parts: edema, necrosis, and actively enhancing regions. A radiologist or other user may interface with the segmentation application 109 in real-time to review and or modify the segmentation because only a portion of the image is being segmented and the whole organ analysis has already been completed by the segmentation models 109A, 109B off-line.

In some embodiments, the deep learning segmentation model 109A employs a convolution neural network (CNN). For example, a CNN based on the 3D U-Net architecture may be used. Briefly, the input image data is set to 128×128×128 voxels, constrained by the limited memory in the GPU. Processing from left to right, the 3D image volume is sequentially reduced in spatial resolution with multiple 3×3×3 convolution layers while increasing the number of filters or feature maps as the levels move deeper. Once the lowest level is reached, the extracted feature maps are then upsampled to sequentially restore the spatial resolution at each level, concatenating with feature maps preserved during the downsampling to help restore lost information. A Softmax function classifies the 3 tumor classes. Dropouts with probability 0.3 are included to minimize overfitting.

To account for the class imbalance, where there is much more background pixel data than tumor, other than cropping, a multiclass Jaccard loss function is used in some embodiments. The four classes include 0 for background, 1 for tumor core, 2 for edema, and 4 for enhancing tumor. A loss function is used:

$$\text{loss} = -\frac{1}{K} \sum_{k \in K} \frac{\sum_i u_i^k v_i^k}{\sum_i u_i^k + \sum_i v_i^k - \sum_i u_i^k v_i^k},$$

where u is the prediction of the CNN and v is from the ground truth segmentation value, i is the pixel number, and k is each class in all K=4 classes. The Jaccard coefficient is a measure of similarity between the segmented prediction and truth image volumes, where higher value indicates greater overlap. The multiclass version is the intersection over union of the two volumes averaged over the four classes. A negative term was added to the loss function to ensure the minimum loss function was optimized. In some embodiments, CNN development uses the open-source machine learning library, TensorFlow, and neural networking API, Keras. Other embodiments may use other machine learning libraries, for example, CNTK.

In some embodiments, the algorithmic segmentation model 109B classifies every organ voxel (e.g., brain voxel) as belonging to one of several tissue types to generate a tissue map 310. For brain tissue, the tissue types include cerebrospinal fluid (CSF), gray matter, white matter, vessels, ventricles, and disease. In some embodiments, gray and white matter are found by performing Bayesian classification of the T1-weighted, contrast-enhanced image using an Expectation Maximization (EM) algorithm. One element of Bayesian classification is the probability that a voxel belongs to a certain tissue class prior to observing its brightness. When this prior probability varies across the image, it is referred to as a spatially-varying prior (SVP). The SVP is estimated through affine registration of the SPM atlas. Rules of logic are applied to the set of all four MR spectra to derive the other tissues. For example, enhancing tumor is described by areas that show hyper-intensity under contrast-enhancement when compared to the non-enhanced image, but also when compared to healthy white matter. The resultant tissue segmentation is used by the segmentation application 109 for anatomic context. For example, the segmentation application 109 may exclude vessels and ventricles from tumor structures.

In some embodiments, the tissue map 310 is used by the segmentation application 109 to refine the boundaries 305 identified by the deep learning segmentation model 309A.

Figure 4:
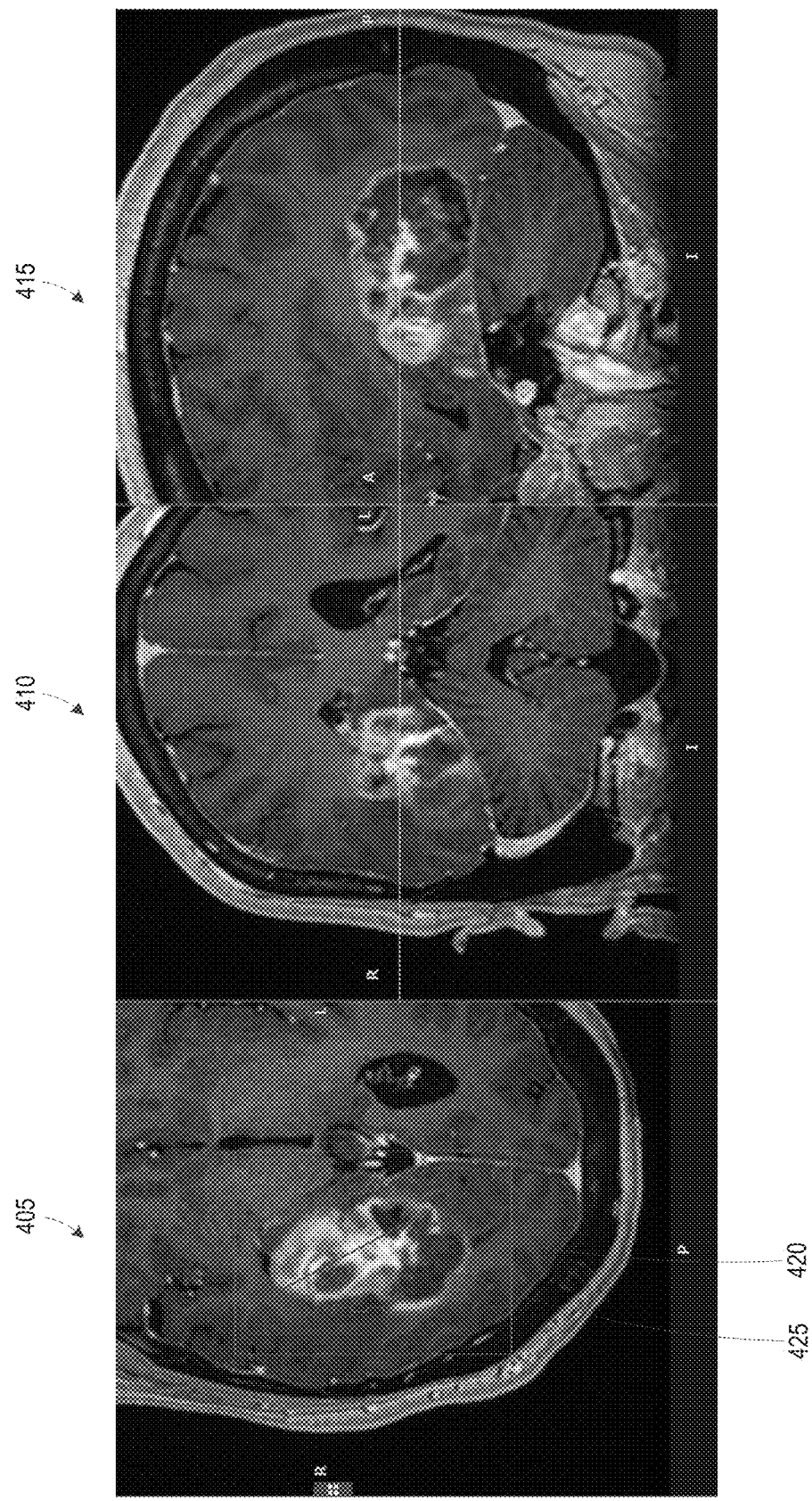
FIGS. 4 and 5 illustrate medical images on which visual indications of planar contours are generated responsive to a user input confirming a candidate structure identified by the segmentation in FIG. 3, according to some embodiments.
Figure 5:
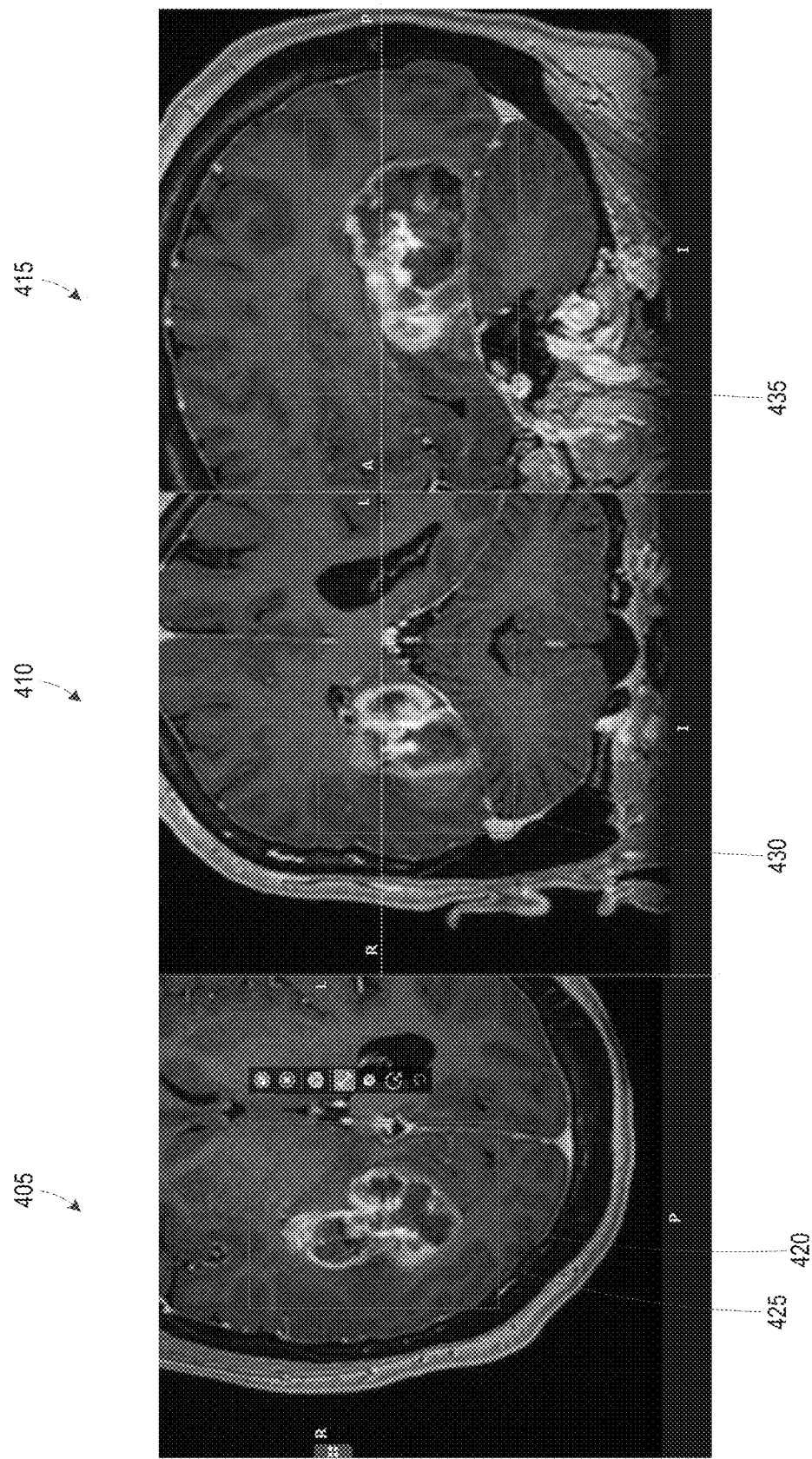

Returning to FIG. 2, in block 215, the segmentation application 109 displays a first planar medical image on the display 101. FIGS. 4 and 5 illustrate medical images on which visual indication of planar contours are generated responsive to a user confirming a candidate structure identified by the segmentation in FIG. 3, according to some embodiments. FIG. 4 illustrates a first medical image 405 (e.g., an axial plane image), a second medical image 410 (e.g., a coronal plane image, and a third medical image 415 (e.g., a sagittal plane image). Initially, the segmentation application 109 displays the medical images 405, 410, 415 without any annotations.

In block 215, the segmentation application 109 receives, via the user interface 103, a user input 420 indicating a region in the first planar medical image. In some embodiments, the user provides the user input 420 by drawing an axis through a region of interest. In some embodiments, the axis is a straight line. The axis may be a long axis, a short axis, or a partial axis. In other embodiments, the user provides the user input 420 by clicking within the region, circling the region, circling a portion of the region, drawing a line in a portion of the region, or the like.

In block 225, the segmentation application 109 determines whether the region identified by the user input in the first planar medical image coincides with a boundary 305 of a candidate structure identified by the segmentation models 109A, 109B. In some embodiments, the user indicates that the user input 420 is complete (e.g., the long axis is drawn as intended), and the segmentation application 109 proceeds with the determination in block 225. In some embodiments, the segmentation application 109 determines whether the region identified by the user input in the first planar medical image coincides with a boundary 305 of a candidate structure by determining whether a long axis drawn by the user has endpoints that intersect or are proximal to the boundary 305. For example, the endpoints of the axis may be within a predetermined distance from the boundary 305. In some embodiments, the segmentation application 109 determines whether the region identified by the user input in the first planar medical image is within a boundary 305 of a candidate structure by determining whether the indicated region coincides with the boundary 305.

Responsive to determining that the region identified by the user input in the first planar medical image is not within the boundary 305 of a candidate structure in block 225, the segmentation application performs user-directed segmentation in block 230. In some embodiments, the tissue map 310 generated by the algorithmic segmentation model 109B is used to facilitate user-directed segmentation.

Responsive to determining that the region identified by the user input in the first planar medical image is within the boundary 305 of a candidate structure in block 225, the segmentation application generates a planar contour 425 of the candidate structure in block 235. In some embodiments, the planar contour 425 is generated by projecting the boundary 305 on the plane corresponding to the first medical image 405. In some embodiments, the segmentation application 109 generates the planar contour 425 prior to determining if the region is within the boundary 305 in block 225 to facilitate the determination.

In block 240, the segmentation application 109 re-displays the first medical image 405 on the display to provide a visual indication of the planar contour 425, as illustrated in FIG. 4. In some embodiments, the segmentation application 109 also generates planar contours 430, 435 for the other medical images 410, 415 by projecting the boundary 305 into the plane corresponding to the particular medical image 410, 415. The planar contours 430, 435 are shown in the medical images 410, 415, as illustrated in FIG. 5. In some embodiments, the planar contours 425, 430, 435 appear more coarsely pixilated because the medical images 405, 410, 415 displays super-sampled images, whereas the deep learning segmentation model 109A operates on full resolution images.

In some embodiments, the segmentation application generates planar contours for other medical images in the set of medical images after receiving the user input. For example, medical images having the same orientation as the medical image 405, but in different slices, may be annotated with planar contours to allow the user to scroll through the slices to see the boundaries of the structure throughout its 3D volume.

In some embodiments, if the user determines that the planar contours 425, 430, 435 are unsatisfactory, the user may draw additional axes or move the envelope defined by the planar contours 425, 430, 435. Data from the deep learning segmentation model 109A and the tissue map 310 generated by the algorithmic segmentation model 109 may be used to alter the boundary 305 and the planar contours 425, 430, 435.

In block 245, the segmentation application generates a finding record for the candidate structure contained within the boundary 305. In some embodiments, a finding record includes a 3-D mesh and metadata describing the characteristics of the mesh. In some embodiments, the finding record is a 3-D image volume. In some embodiments, the user indicates that the candidate structure contained within the boundary 305 identified by the segmentation application 109 (e.g., using the deep learning segmentation model 109A) is a valid finding.

If the user identifies multiple structures of interest in the medical images 405, 410, 415, the method 200 may be repeated for each structure. Since the candidate structures are not initially provided to the user, the user is not burdened with false positives. Only those candidate structures that correspond to findings indicated by the user are presented.

In the foregoing specification, specific embodiments have been described. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of present teachings.

Various features and advantages of some embodiments are set forth in the following claims.

What is claimed is:

1. A system for volumetric segmentation in a plurality of planar medical images, comprising:
   a display;
   a user interface;
   an electronic processor coupled to the display and the user interface; and
   memory coupled to the electronic processor and storing instructions that, when executed
   by the electronic processor, cause the system to:
      receive the plurality of planar medical images;
      generate a boundary of a candidate structure in the plurality of medical images using a segmentation model;
      displaying, on the display, a first planar medical image from the plurality of planar medical images;
      receive, by the user interface, a user input indicating a region in the first planar medical image;
      generate a first planar contour of the candidate structure;
      compare the region to the boundary; and
      responsive to the region being at least partially within the boundary:
         re-display, on the display, the first planar medical image showing the first planar contour of the structure; and
      generate a finding record for the candidate structure including the boundary.

2. The system of claim 1, wherein the instructions, when executed by the electronic processor, cause the system to:
   generate the finding record responsive to receiving a user input accepting the first planar contour.

3. The system of claim 1, wherein the user input comprises an axis drawn on the first planar medical image.

4. The system of claim 3, wherein the instructions, when executed by the electronic processor, cause the system to:
   compare the region to the boundary by determining if endpoints of the axis are within a predetermined distance from the boundary.

5. The system of claim 3, wherein the instructions, when executed by the electronic processor, cause the system to:
   compare the region to the boundary by determining if endpoints of the axis are within a predetermined distance from the first planar contour.

6. The system of claim 1, wherein the instructions, when executed by the electronic processor, cause the system to:
   generate a second planar contour of the candidate structure; and
   display a second medical image of the plurality of medical images showing the second planar contour, wherein the first and second medical images are associated with different plane orientations.

7. The system of claim 6, wherein the first planar medical image is associated with one of an axial plane, a coronal plane, or a sagittal plane, and the second medical image is associated with a different one of the axial plane, the coronal plane, or the sagittal plane.

8. The system of claim 6, wherein the first planar medical image is associated with one of an axial plane, a coronal plane, or a sagittal plane, and the second medical image is associated with the same one of the axial plane, the coronal plane, or the sagittal plane.

9. The system of claim 1, wherein the segmentation model comprises a deep learning segmentation model.

10. The system of claim 1, wherein the segmentation model comprises an algorithmic segmentation model.

11. A method for volumetric segmentation in a plurality of planar medical images, comprising:
   receiving, at an electronic processor, the plurality of planar medical images;
   generating a boundary of a candidate structure in the plurality of medical images using a segmentation model;
   displaying, on a display, a first planar medical image from the plurality of planar medical images;
   receiving, by a user interface, a user input indicating a region in the first planar medical image;
   generating a first planar contour of the candidate structure;
   comparing the region to the boundary; and
   responsive to the region being at least partially within the boundary:
      re-displaying, on the display, the first planar medical image showing the first planar contour of the structure; and
   generating a finding record for the candidate structure including the boundary.

12. The method of claim 11, comprising:
   generating the finding record responsive to receiving a user input accepting the first planar contour.

13. The method of claim 11, wherein receiving, by the user interface, the user input comprises receiving an axis drawn on the first planar medical image.

14. The method of claim 13, wherein comparing the region to the boundary comprises determining if endpoints of the axis are within a predetermined distance from the boundary.

15. The method of claim 13, wherein comparing the region to the boundary comprises determining if endpoints of the axis are within a predetermined distance from the first planar contour.

16. The method of claim 11, comprising:
   generating a second planar contour of the candidate structure; and
   displaying a second medical image of the plurality of medical images showing the second planar contour, wherein the first and second medical images are associated with different plane orientations.

17. The method of claim 16, wherein the first planar medical image is associated with one of an axial plane, a coronal plane, or a sagittal plane, and the second medical image is associated with a different one of the axial plane, the coronal plane, or the sagittal plane.

18. The method of claim 16, wherein the first planar medical image is associated with one of an axial plane, a coronal plane, or a sagittal plane, and the second medical image is associated with the same one of the axial plane, the coronal plane, or the sagittal plane.

19. The method of claim 11, wherein the segmentation model comprises a deep learning segmentation model.

20. The method of claim 11, wherein the segmentation model comprises an algorithmic segmentation model.

* * * * *